US006110380A

United States Patent [19]

Barbera-Guillem

[11] Patent Number: 6,110,380

[45] **Date of Patent: *Aug. 29, 2000**

[54] DEVICE AND METHOD FOR MAGNETIC SEPARATION OF BIOLOGICAL MOLECULES

[75] Inventor: Emilio Barbera-Guillem, Powell, Ohio

[73] Assignee: BioCrystal Ltd., Westerville, Ohio

[ * ] Notice: This patent is subject to a terminal disclaimer.

[21] Appl. No.: 09/079,469

[22] Filed: May 15, 1998

[51] Int. Cl.$^{7}$ .............................. B01D 35/06; B03C 1/00; C12N 13/00

[52] U.S. Cl. .......................... 210/695; 210/222; 210/223; 209/213; 96/1; 435/2; 435/7.21; 435/173.1; 435/261; 435/803; 436/526; 436/824

[58] Field of Search .................................... 210/222, 223, 210/695; 209/213; 96/1; 428/355 R; 435/2, 7.21, 173.1, 261, 803; 436/526, 824

[56] References Cited

U.S. PATENT DOCUMENTS 4,910,148 3/1990 Sorensen et al. .
5,078,871 1/1992 McCready ............................... 210/222
5,663,241 9/1997 Takamatsu et al. ................ 428/355 R

*Primary Examiner*—David A. Reifsnyder
*Attorney, Agent, or Firm*—M. Bud Nelson

[57] ABSTRACT

Provided is a magnetic separation device comprising a container having one or more outer surfaces; at least one flexible magnetic sheet; and a non-permanent adhesive that is used to detachably secure an outer surface of the container to a flexible magnetic sheet. A method of using the magnetic separation device according to the present invention comprises obtaining a fluid containing a mixed population of biological molecules, from which it is desired to separate at least one subpopulation of biological molecules; mixing the fluid with a magnetic separation reagent; contacting the mixture with the fluid holding chamber of the magnetic separation device; incubating the mixture for a sufficient time to allow for complexes to form between the subpopulation of biological molecules and the magnetic separation reagent; positioning the magnetic separation device in a position that magnetically attracts the complexes towards the flexible magnetic sheet, and thereby holds them in position in the container; and removing the remainder of the fluid from the magnetic separation device.

46 Claims, 6 Drawing Sheets

DEVICE AND METHOD FOR MAGNETIC SEPARATION OF BIOLOGICAL MOLECULES

FIELD OF THE INVENTION

The present invention generally relates to devices and methods for magnetic separation of one or more targeted molecules present in a solution comprising a mixed population of molecules. More particularly, the present invention relates to separation of target biological molecules using magnetic particles and a magnetic separation device.

BACKGROUND OF THE INVENTION

There are various methods available to isolate or separate biological molecules such as cells, antibodies, antigens, proteins, carbohydrates, nucleic acids, and the like. Magnetic separation techniques typically involve the application of a magnetic field to separate ferromagnetic particles contained within a fluid medium. Such techniques use devices that can be divided into two general types: an internal apparatus, or an external apparatus. In the internal apparatus, the ferromagnetic collection structure is contained within the fluid medium in order to intensify the applied magnetic field and improve the resultant gradient. One example of an internal apparatus involves packing steel wool or wires ("collection structures") into a column, wherein the column is situated adjacent to a magnet. A magnetic field is applied to the steel wires such that magnetic particles introduced into the column are attracted toward, and bind to, the steel wires. Another example of an internal apparatus involves loops of ferromagnetic wire that are inserted into a fluid medium. Drawbacks of such systems include entrapment of non-magnetic components; the potential for magnetic shielding of the collection structure therein; breakage of the collection structure during use and/or cleaning, and the requirement for cleaning or disposal of the collection structure between samples. In the external apparatus, generally the magnetic means is situated entirely externally with respect to the separation chamber. Typically, an external apparatus involves a plurality of magnets, or complex magnetic circuitry, placed around the periphery of the separation chamber; wherein the plurality of magnets, or the magnetic circuitry, produces a magnetic field gradient used to effect the magnetic separation. Drawbacks of the external systems include the need for intervention by the user to redesign the placement, positioning, or sizing of the plurality of magnets or circuitry to apply a magnetic field gradient to separation chambers of different sizes; and the additional need for manipulating multiple structures required for placement and positioning of the plurality of magnets or magnetic circuitry.

It is desirable, therefore, to provide a device for magnetic separation of components in a fluid that minimizes the amount of intervention necessary from a user. Additionally, it is desirable to provide a device for magnetic separation of components in a fluid that obviates the need for multiple structures for operation of the magnetic separation, and the manipulation associated with such structures.

SUMMARY OF THE INVENTION

It is an object of the present invention to provide a magnetic separation device that is simple to use, and provides a means for achieving rapid, high yield, and high purity of a selected biological molecule.

It is another object of the invention to provide a magnetic separation device that can be used to separate a biological molecule comprising a cell subpopulation of interest from a mixed population of cells in a fluid.

It is another object of the invention to provide a magnetic separation device that can be used to separately isolate more than one selected biological molecule of interest from a mixed population of biological molecules in a fluid. When the biological molecule comprises a cell subpopulation, the magnetic separation device may be used to separately isolate more than one cell subpopulation of interest from a mixed population of cells in a fluid.

It is further object of the invention to provide a magnetic separation device that may be available in a variety of sizes to provide a efficient and economical means for achieving rapid, high yield, and high purity of a selected biological molecule in a fluid.

It is an additional object of the invention to provide magnetic separation methods that are simple to use, and provide means for achieving rapid, high yield, and high purity of a selected biological molecule.

It is another object of the invention to provide magnetic separation methods that can separately isolate more than one selected biological molecule of interest from a mixed population of biological molecules in a fluid. When the biological molecule comprises a cell subpopulation, the magnetic separation methods may separately isolate more than one cell subpopulation of interest from a mixed population of cells (and non-cellular biological molecules) in a fluid.

According to one aspect of the invention, the magnetic separation device comprises a container means having at least one side or face with an outer surface which is substantially flat, and to which outer surface is detachably secured in a face to face manner a flexible magnetic sheet means using a non-permanent adhesive. According to another aspect of the invention, a fluid containing a mixed population of biological molecules, and magnetic particles coated with a ligand (magnetic separation reagent) having sufficient binding specificity and affinity for the target biological molecule (the molecule desired to be isolated from the fluid) for achieving magnetic separation, are introduced into the container means of the magnetic separation device. The magnetic separation reagent contacts and binds, via the ligand coating, with the target biological molecule present in the fluid in forming complexes. These complexes are drawn to, by magnetic attraction, and contact the inside of the face of container means, the outer surface of which is detachably secured to the flexible magnetic sheet means. After a sufficient time for contact and binding interactions between the magnetic separation reagent and the target biological molecule in forming complexes, the fluid is removed thereby achieving either negative selection (wherein the separated target biological molecule is discarded) or positive selection (wherein the separated target biological molecule is to be retained). In positive selection, the inner surfaces of the container means of the magnetic separation device may be washed to remove any remaining unbound biological molecules, while the target biological molecule remains bound, via magnetic attraction, as part of the complex with the magnetic separation reagent. A final fluid medium is introduced into the container means, and the flexible magnet sheet means is then removed from the container means by a peeling action, thereby removing the magnetic force holding the complexes in place in the container means and thereby releasing the complexes into the final fluid medium. The separated biological molecule may then be harvested from the complexes, if desired.

The above and other objects, features, and advantages of the present invention will be apparent in the following Detailed Description of the Invention when read in conjunction with the accompanying drawings in which reference numerals denote the same or similar parts throughout the several illustrated views and embodiments.

DETAILED DESCRIPTION OF THE INVENTION

Definitions

Figure 1:
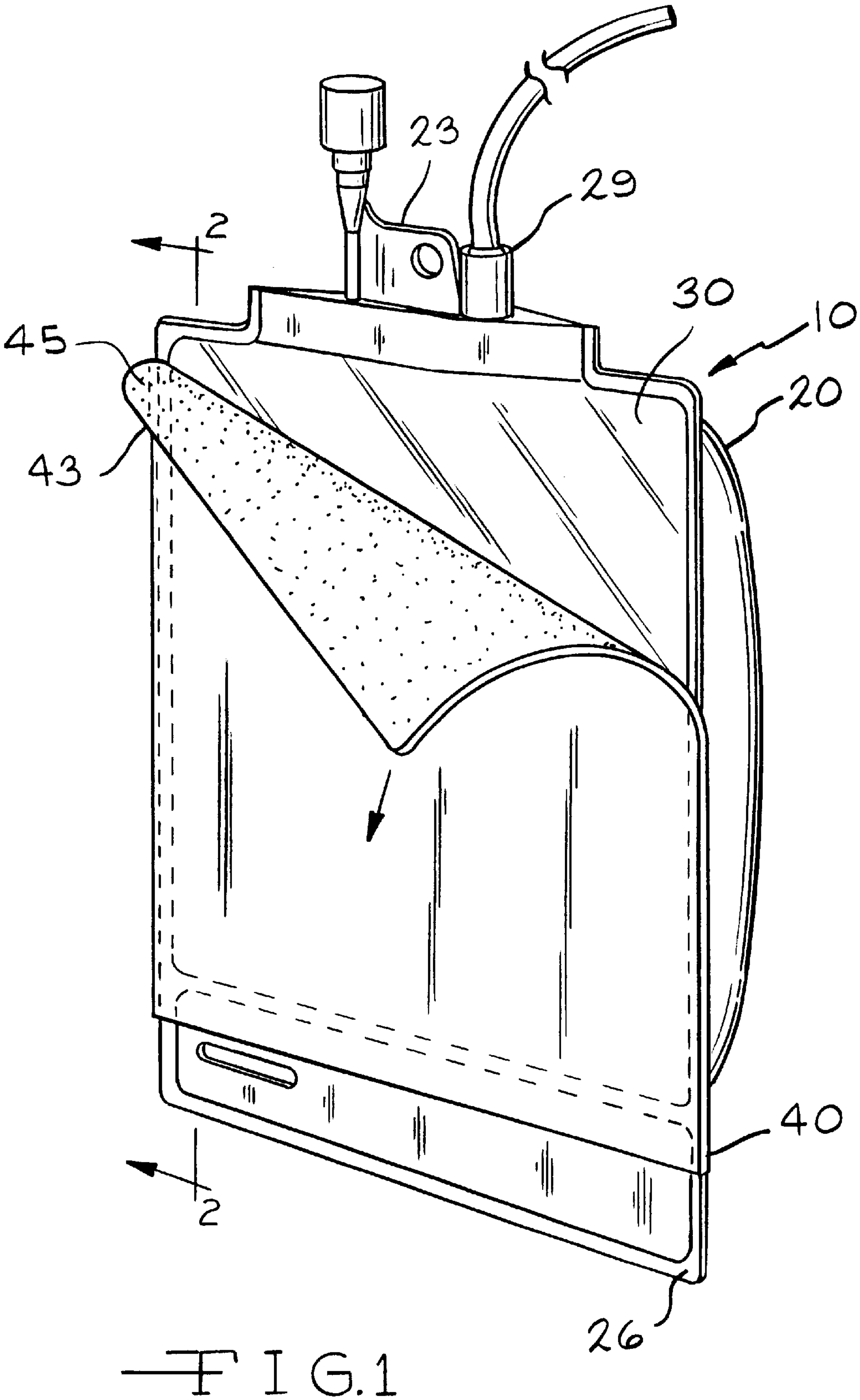
FIG. 1 is a perspective view of the magnetic separation device, wherein the flexible magnetic sheet means and the container means are peeled apart to expose the non-permanent adhesive.

The term "biological molecule" is used herein, for purposes of the specification and claims, to mean a substance including, but not limited to, eukaryotic cells; prokaryotic cells; and complex molecules such as proteins, glycoproteins, lipoproteins, peptides, carbohydrates, lipids, nucleic acid molecules, and drugs. The term "ligand" when used in conjunction with a biological molecule is used herein, for purposes of the specification and claims, to mean a substance coating a magnetic particle which has binding specificity (to the substantial exclusion of other substances) and avidity for a biological molecule. Ligands are known to those skilled in the art to include antibodies, antibody fragments that retain binding activity ($F(ab')_2$, Fab', Fab, Fv, scFV, Fd' and Fd fragments); lectins; selectins; agglutnins; receptors (cell-associated or acellular); complementary nucleic acid sequences (e.g. anti-sense or oligonucleotide probes) and other molecules which are capable of binding to a specific cell subpopulation or species of complex molecules. For example, and as known to those skilled in the art, a magnetic particle may be coated with a ligand that comprises a monoclonal antibody. Such a monoclonal antibody, when having binding specificity and avidity for a particular type of tumor cell (e.g., expressing a certain cell-associated tumor specific marker), can be used to bind substantially all cells of that particular tumor type (e.g., binding to cells expressing the tumor specific marker on their surface) that may be present in a fluid, thereby allowing for removal or isolation of that cell subpopulation from the fluid by magnetic separation. The term "magnetic separation reagent" is used herein, for purposes of the specification and claims, to mean magnetic particles coated with a specific ligand for the purpose of separating a specific subpopulation of ("target") biological molecule from a mixed population of biological molecules in a fluid using the device and method according to the present invention for magnetic separation.

The term "complexes" is used herein, for purposes of the specification and claims, to mean the magnetic separation reagent having bound thereto, via the ligand, target biological molecules.

The term "container" or "container means" is used herein, for purposes of the specification and claims, to mean a chamber for holding a fluid, wherein the chamber has at least two walls or outer surfaces; and at least one aperture comprising an inlet to allow for the introduction of one or more substances into the container, or an outlet for withdrawal or removal of one or more substances from the container, or a combination of both, and wherein the at least one aperture is closable or sealable to prevent the contents inside the container from leaking out of the container. The container may be in the form including, but not limited, to a flexible bag ("bag means"), such as a medical fluid bag, cell culture bag, or blood collection bag; and a flask or bottle, such as for collecting medical specimens or culturing cells. The composition of the container may be of a thermoplastic polymer, of high ethylene vinyl acetate polymer content, a flexible synthetic resin, or other suitable material having properties compatible with its intended purpose. Flexible bags are known in the art to be made of materials such as polyvinyl chloride, polyolefins (e.g., polypropylene), polyurethanes, and the like. In a preferred embodiment of the invention, the container is comprised of a material sufficiently clear enough to allow a user to visually observe the contents of the container, and manipulations of the contents therein.

The term "flexible magnetic sheet" or term "flexible magnetic sheet means" is used herein, for purposes of the specification and claims, to mean a substantially flat sheet having a magnetic field of sufficient strength to attract, and securedly hold into position, magnetic particles or magnetic separation reagent or complexes placed adjacent thereto; and of a sufficient pliability to allow for the flexible magnetic sheet means of the magnetic separation device according to the present invention to be separated from the container means using a peeling action, as will be more apparent from the following examples. The flexible magnetic sheet may be opaque, or transparent, depending on its composition. A flexible magnetic sheet includes, but is not limited to, a thin flexible magnetic sheet consisting of a fine magnetic powder such as barium ferrite loaded into a thermoplastic binder; a thin flexible sheet of plastics or vinyl material impregnated with a ferromagnetic material; a synthetic resin material having mixed therein a magnetic powder; magnetic particles embedded in a flexible polymer sheet of typically 0.7 mm or 0.030 inches thickness; and a vinyl material including magnetic materials dispersed therethrough. An example of a flexible magnetic sheet that can be commercially purchased, and that is useful in making the magnetic separation device according to the present invention, is available under the trademark "ProMag" from Magnetic Specialty, Inc., Marietta, Ohio. Commercially available examples of a flexible magnetic sheet have a magnetic field strength in a range which includes, but is not limited to, about 150 to about 600 Gauss.

The term "magnetic particle" is used herein, for purposes of the specification and claims, to mean particles known in the art currently or in the future, which can be used to achieve magnetic separation by responsiveness and attraction to a magnetic field. Magnetic particles, also known in the art as magnetic spheres or magnetic beads or microclusters, comprise one or more compounds including, but not limited to, a core comprising one or more metals, metal oxides, metal alloys, metal salts, metal organic particles, metal hydroxides, and mixed lattices thereof. Inorganic cores are known in the art to be comprised of iron, cobalt, nickel, ferric oxide, nickel oxide, cobaltic oxides, and ferrites. Additionally, the magnetic particle may also be comprised of a polymeric coating for attachment to biological materials, a biodegradable coating, and/or another functional type of coating that may be useful or advantageous in magnetic separation. Biodegradable coatings on magnetic particles are known to those skilled in the art (for a review, see, e.g., U.S. Pat. No. 5,707,877; U.S. Pat. No. 5,382,468).

The term "non-permanent adhesive" is used herein, for purposes of the specification and claims, to mean a "removable" adhesive of a sufficiently low tack that allows the flexible magnetic sheet means of the magnetic separation device according to the present invention to be removed from the container means, as will be more apparent from the following embodiments. That is, the non-permanent adhesive is an adhesive of adequate peel strength to allow for the flexible magnetic sheet means to be peeled away from the container means, without substantially damaging surfaces of either the container means and flexible magnetic sheet means when they are peeled apart from each other. Further, the adhesive is of an initial and appropriate cohesive strength to control and inhibit the substantial transfer of adhesive residue to a surface other than the surface onto which it is specifically layered. The non-permanent adhesive may be in the form of a double-faced adhesive tape, a polymeric adhesive, a pressure-sensitive acrylic adhesive, rubber cement, or any other form of adhesive useful for the purposes attendant to the present invention, as will be more apparent in the following descriptions. Double-faced adhesive tapes are known in the art to have adhesives on both sides of a film, wherein the film functions as a support onto which is applied the adhesives.

In a preferred embodiment, the non-permanent adhesive comprises a "repositionable" adhesive which allows for the flexible magnetic sheet means to be removed from the container means; and additionally if desired, following removal, allows for the flexible magnetic sheet means to be repositioned with respect to the container means, and reapplied in a detachably secured manner with the application of light pressure to the container means or flexible magnetic sheet. Repositionable adhesives can be repeatedly adhered to and removed from a substrate without substantial loss of adhesion capacity (for a review of such adhesives, see, e.g., U.S. Pat. No. 5,663,241). An example of a high performance acrylic based pressure sensitive adhesive useful in making the magnetic separation device according to the present invention is commercially available under the product name "MACbond IB-2101" by MACtac, Inc., Stow, Ohio.

EXAMPLE 1

In this example, illustrated are various embodiments of the magnetic separation device according to the present invention.

In its simplest form, the magnetic separation device 10 of the present invention is comprised of three main components, as illustrated in FIGS. 1–5. The magnetic separation device 10 comprises a container means 20 having at least one face or side 30, the outer surface of face 30 being substantially flat. Container means 20 is removably attached to flexible magnetic sheet means 40 by nonpermanent adhesive 45. That is, non-permanent adhesive 45 may be applied to and form a coat on a surface selected from the group consisting of an outer surface of side 30 of container means 20 (see, e.g., FIGS. 3 & 4), a face 43 of flexible magnetic sheet means 40 to be engaged by side 30 (see, e.g., FIGS. 1 & 5), or a combination thereof. To the outer surface of side 30 is detachably secured over a substantial means of side 30 a flexible magnetic sheet means 40 such that container means 20 and flexible magnetic sheet 40 meet in a face to face manner in being assembled together to form magnetic separation device 10. Typically, the magnetic separation device will comprise a single unit. However, also encompassed herein by the term "magnetic separation device" is a magnetic separation device that is part of a multiple unit. As illustrated in FIG. 6 by way of example, the multiple unit may comprise a plurality of magnetic separation devices which are physically connected in tandem, but which may be manipulated to maintain a separate chamber per magnetic separation device. Alternatively, a multiple unit may comprise a magnetic separation device physically connected to a plurality of container means. The series of container means are physically connected in tandem, and may be manipulated to maintain a separate chamber per container. The flexible magnetic sheet may be removed from a first magnetic separation device of the multiple unit, after a first selection process, and applied (by means of a non-permanent adhesive) and detachably secured to one of the container means in the plurality of container means to form a second magnetic separation device for a second selection process. Thus, the flexible magnetic sheet may be applied to, and may be used for, each container means of the pluarilty of container means. The multiple unit, may also have at least one separate aperture specific for each respective container means in the multiple unit.

In the embodiment shown in FIG. 1, container means 20 comprises a bag means capable of holding a fluid. Examples of such bags include, but are not limited to, blood collection bags, cell culture bags, or medical solution bags. Because a conventional assortment of such bags are used by those skilled in the art, wherein the assortment of bags differ in size and therefore fluid capacity as well as overall length and width, it will be appreciated, of course, that the dimensions of bag means 20 represented in FIGS. 1–4, and others which are subsequently given herein, are merely for purposes of explanation and illustration, and are not intended to limit the invention in any way. For example, standard or conventional sizes of such bags include a size for fluid capacities ranging from approximately 30 ml to approximately 100 ml; a size for fluid capacities ranging from approximately 150 ml to approximately 500 ml, and a size for fluid capacities ranging from approximately 300 ml to 1500 ml. However, custom size bags (e.g., for fluid capacities less than 30 ml) can be easily manufactured using methods and materials known to those skilled in the art.

In a preferred construction, bag means 20 comprises a walled housing means with at least one aperture 29 through which a fluid may be introduced into, and/or removed from, bag 20. Bag 20 has a side or face 30 the outer surface of which is substantially flat. Detachably secured over a substantial means of the outer surface of face 30 is flexible magnetic sheet 40 such that bag 20 and flexible magnetic sheet 40 meet in a face (30) to face (43) manner in being assembled together to form magnetic separation device 10. The flexible magnetic sheet 40 and the side 30 of bag 20 to which it is detachably secured are generally, but not necessarily, dimensionally coextensive in length, width, and shape. In a preferred embodiment, flexible magnetic sheet 40 is generally dimensionally coextensive in length, width, and shape with that section of bag 20 along side 30 which comprises the fluid holding chamber of bag 20; thereby maximizing the functional surface area along side 30 available for magnetic separation reagent and/or complexes to bind. In a preferred embodiment, when the container is a bag means, a portion of the bag 20 extends beyond the dimensional margins of the flexible magnetic sheet 40 such that the user can readily grip the extended portion of the bag 20 to start the peeling action when it is desired to separate the bag from the flexible magnetic sheet, as shown in FIGS. 1–4. For example, one standard size for a bag having a fluid capacity of approximately 30 to 60 ml is about 6 inches in width (side to side) and 8 inches in height (top 23 to bottom 26).

In continuing with this example, and with reference to FIG. 1, a flexible magnetic sheet 40 of about 6 inches in width and 6 inches in height is detachably secured to bag means 20 so as to be generally dimensionally coextensive in length, width, and shape (with the fluid holding chamber of bag means 20). With continuing reference to FIG. 1, non-permanent adhesive 45 is applied to, and forms a coat on, surface 43 of flexible magnetic sheet 40. Pressure is applied to bag 20 and/or flexible magnetic sheet 40 where they are dimensionally coextensive in detachably securing bag 20 to flexible magnetic sheet 40 in a face to face manner thereby forming magnetic separation device 10 (see also, FIG. 2). FIG. 1 shows the flexible magnetic sheet 40 being peeled away from bag means 20 (see arrow) as would be performed in the method of using magnetic separation device 10 when it is desired to release complexes formed therein. Additionally, FIG. 1 shows the flexible magnetic sheet 40 being peeled away from bag means 20 (see arrow) for the additional purpose of showing non-permanent adhesive 45 as applied to, and remaining substantially bonded to, face 43 of flexible magnetic sheet 40.

Figure 3:
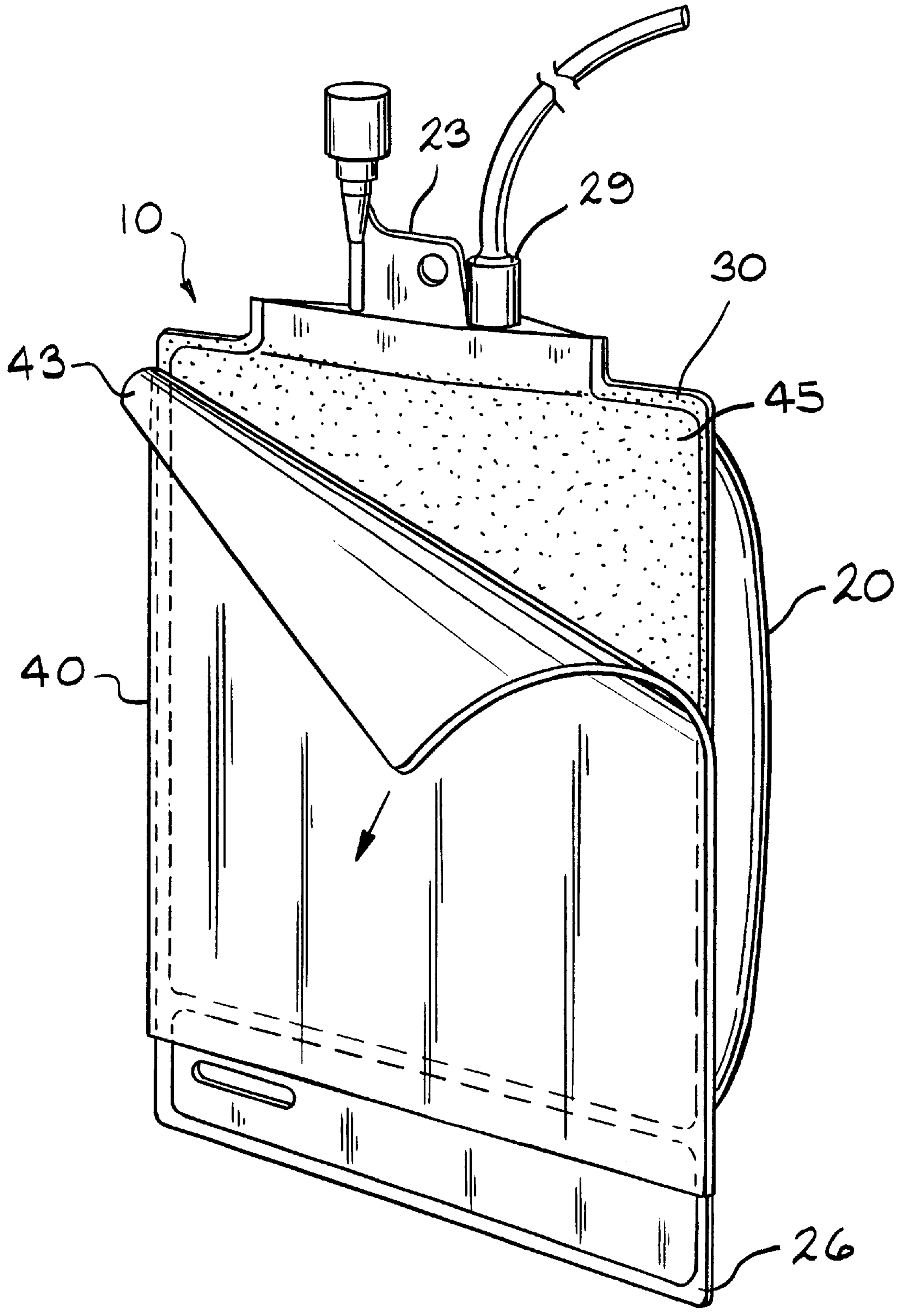
FIG. 3 is a perspective view of another embodiment of the magnetic separation device, wherein the flexible magnetic sheet means and the container means are peeled apart to expose the non-permanent adhesive.

In an additional preferred construction as illustrated in FIG. 3, the bag 20 comprises a walled housing means with at least one aperture 29 through which a fluid may be introduced into, and/or removed from, bag 20. Bag 20 has a side or face 30 the outer surface which is substantially flat. Detachably secured over a substantial portion of the outer surface of face 30, is flexible magnetic sheet 40 such that bag 20 and flexible magnetic sheet 40 meet in a face (30) to face (43) manner in being assembled together to form magnetic separation device 10. The flexible magnetic sheet 40 and the side 30 of bag 20 to which it is detachably secured are generally dimensionally coextensive in length, width, and shape (especially in relation with the fluid holding chamber of bag means 20). Bag 20 may, but does not necessarily have to, extend beyond the dimensional margins of the flexible magnetic sheet 40 such that the user can readily grip the extended portion of the bag 20 to start the peeling action (see arrow) when it is desired to separate bag 20 from the flexible magnetic sheet 40. For example, a standard size for a bag having a fluid capacity of between 100 ml to 150 ml is about 9 inches in width (side to side) and about 10 inches in height (top 23 to bottom 26).

Figure 4:
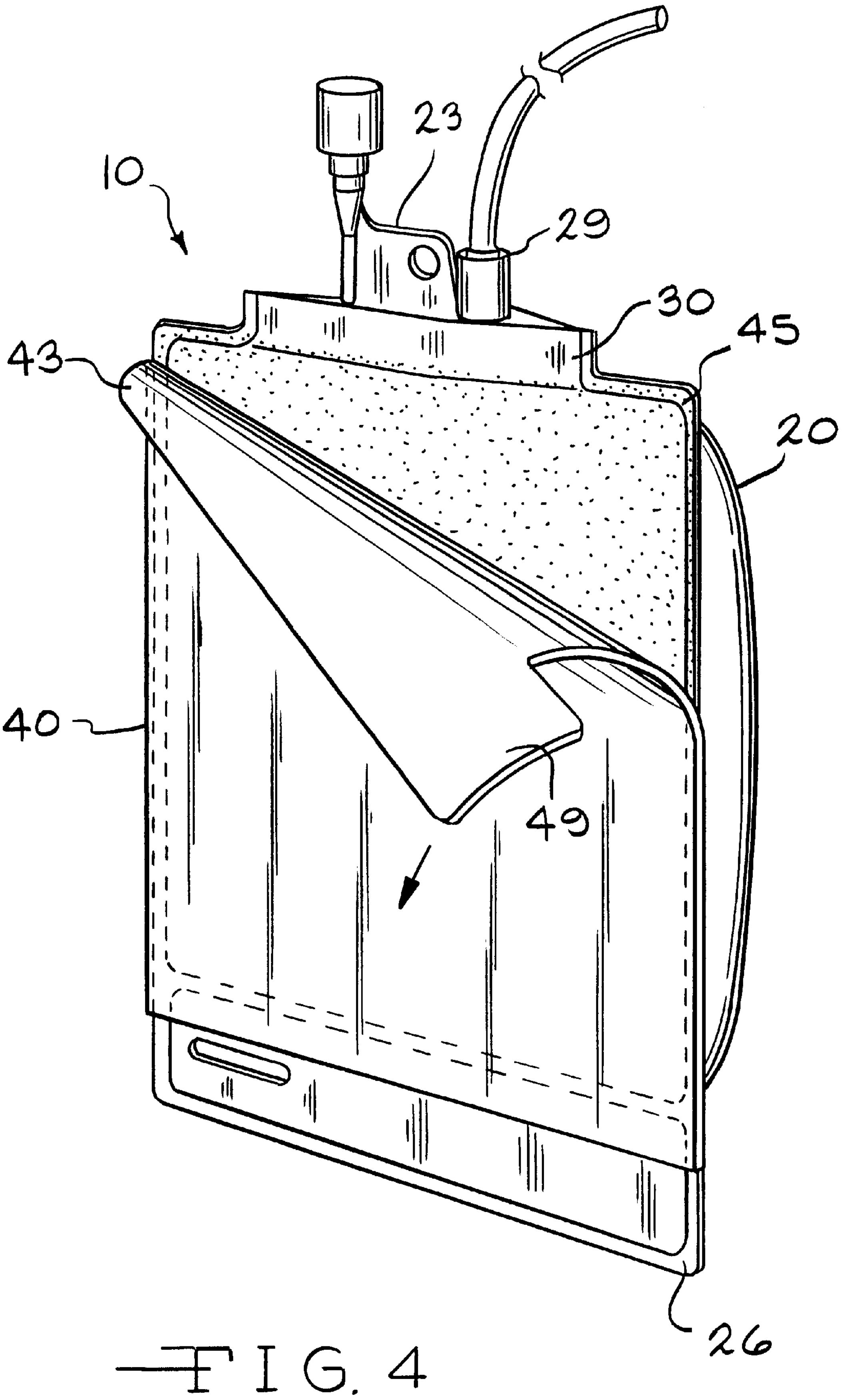
FIG. 4 is a perspective view of an additional embodiment of the magnetic separation device, wherein the flexible magnetic sheet means and the container means are peeled apart to expose the non-permanent adhesive.

In continuing with this example, and with reference to FIG. 3, a flexible magnetic sheet 40 of about 9 inches in width and about 9 inches in height can detachably secured to bag means 20 so as to be generally dimensionally coextensive in length, width, and shape; particularly in relation to the fluid holding chamber of bag means 20. With continuing reference to FIG. 3, non-permanent adhesive 45 is applied to, and forms a coat on, surface 30 of bag 20. Pressure is applied to bag 20 and/or flexible magnetic sheet 40 where they are dimensionally coextensive in detachably securing bag 20 to flexible magnetic sheet 40 in a face to face manner thereby forming magnetic separation device 10. FIG. 3 shows the flexible magnetic sheet 40 being peeled away from bag means 20 (see arrow) as would be performed in the method of using magnetic separation device 10 when it is desired to release complexes formed therein. Additionally, FIG. 3 shows the flexible magnetic sheet 40 being peeled away from bag means 20 (see arrow) for the additional purpose of showing non-permanent adhesive 45 as applied to, and remaining substantially bonded to, face 30 of bag 20. FIG. 4 illustrates an embodiment similar to the magnetic separation device illustrated in FIG. 3. However, magnetic separation device 10, as illustrated in FIG. 4, comprises a flexible magnetic sheet 40 having a radially projecting portion, such as tab means 49, so that the user can readily grip radially projecting tab 49 to facilitate pulling apart or disengaging flexible magnetic sheet 40 from bag 20 by the application of a relatively small force in utilizing a "peeling" action (see arrow) when it is desired to separate flexible magnetic sheet 40 from bag 20.

Figure 5:
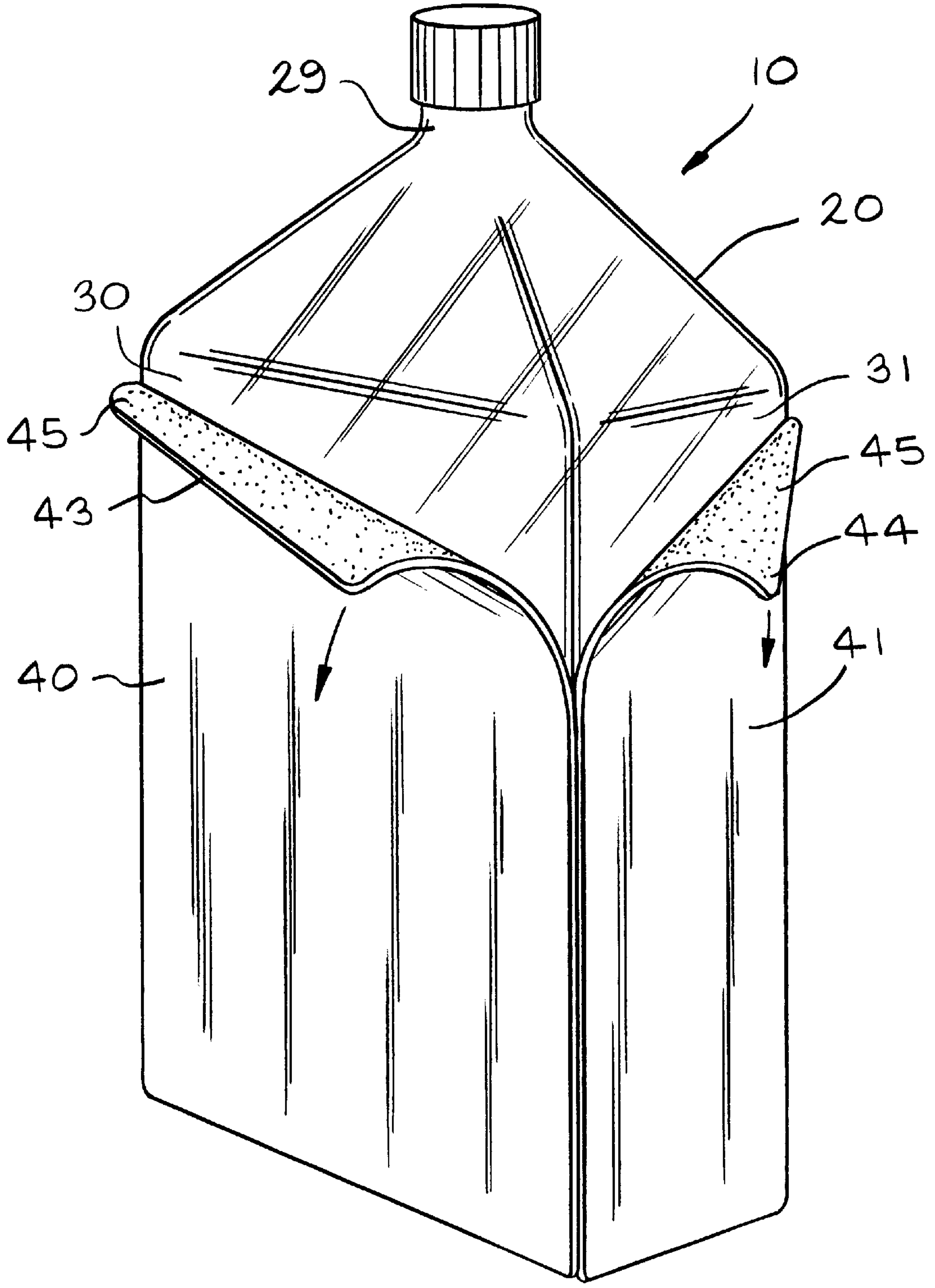
FIG. 5 is a perspective view of the magnetic separation device, showing multiple flexible magnetic sheet means in relation to the container means, which are peeled apart to expose the non-permanent adhesive.
Figure 6:
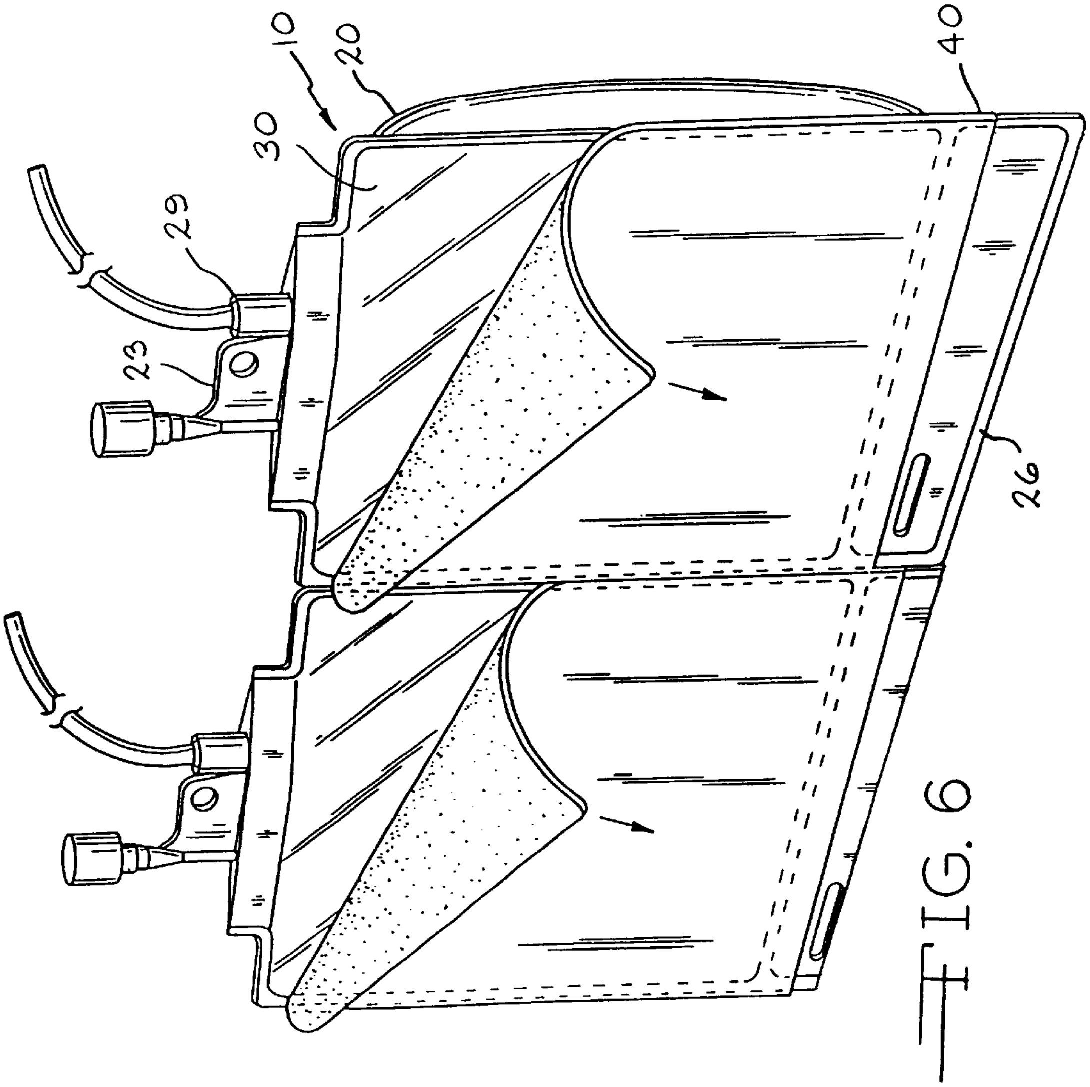
FIG. 6 is a perspective view of an embodiment of a multiple unit of magnetic separation devices.

In a further preferred construction as illustrated in FIG. 5, magnetic separation device 10 comprises a container means detachably secured to at least one flexible magnetic sheet means by a non-permanent adhesive. In this embodiment, the container means can either be a bag means or bottle means. Importantly, depending on the number of sides of the container means, multiple flexible magnetic sheets may be detachably secured to the container means (e.g., one flexible magnetic sheet per side of the container means) thereby allowing for multiple magnetic separations to be performed as will be more apparent in the following embodiments. With further reference to FIG. 5, container means is a bottle means 20 comprising a walled housing means with at least one aperture 29 through which a fluid may be introduced into, and/or removed from, bottle 20. Bottle 20 has one or more sides or faces 30 and 31, the outer surfaces of which are substantially flat. Detachably secured over a substantial portion of each of the outer surfaces of faces 30 and 31 are flexible magnetic sheets 40 and 41 such that bottle 20 and flexible magnetic sheets 40 and 41 meet in a face to face manner in being assembled together to form magnetic separation device 10. The flexible magnetic sheet 40, and side 30 of bottle 20 to which it is detachably secured, are generally dimensionally coextensive in length, width, and shape; particularly in relation to the fluid holding chamber of bottle 20. The flexible magnetic sheet 41, and side 31 of bottle 20 to which it is detachably secured, are generally dimensionally coextensive in length, width, and shape; particularly in relation to the fluid holding chamber of bottle 20 along sides 30 and 31. Bottle 20 may, but does not necessarily have to, extend beyond the dimensional margins of the flexible magnetic sheets 40 and 41, thereby allowing a user to readily grip the flexible magnetic sheets 40 and 41 to start the peeling action (see arrow) when it is desired to separate bottle 20 from either or both of the flexible magnetic sheets 40 and 41.

In continuing with this example, two flexible magnetic sheets 40 and 41 are detachably secured to bottle means 20 so as to be generally dimensionally coextensive in length, width, and shape, in forming magnetic separation device 10. A non-permanent adhesive may be applied to and form a coat on a surface selected from the group consisting of an outer surface (30 and/or 31) of bottle 20, a face of the flexible magnetic sheet (43 and/or 44), or a combination thereof. With continuing reference to FIG. 5, non-permanent adhesive 45 is applied to, and forms a coat on, face 44 of flexible magnetic sheet 41; and is applied to, and forms a coat on, face 43 of flexible magnetic sheet 40. Pressure is applied along the dimensions of flexible magnetic sheets 40 and 41 in detachably securing bottle means 20 to flexible magnetic sheets 40 and 41 in a face to face manner thereby forming magnetic separation device 10. FIG. 5 shows the flexible magnetic sheets 40 and 41 being peeled away from bottle means 20 (see arrows) as would be performed in the method of using magnetic separation device 10 when it is desired to release complexes formed therein. Additionally, FIG. 5 shows the flexible magnetic sheets 40 and 41 being peeled away from bottle means 20 (see arrows) for the additional purpose of showing non-permanent adhesive 45 as applied to, and remaining substantially bonded to, face 43 of flexible magnetic sheet 40, and face 44 of flexible magnetic sheet 41.

It will be apparent to those skilled in the art from the descriptions herein that various modifications can be made of the embodiment illustrated in FIG. 5. For example, since bottle means 20 has four main sides, the number of flexible magnetic sheets that may be detachably secured to bottle means 20 may range from one to four, depending on if multiple magnetic separations are to be performed, and how many magnetic separations are to be performed, using the magnetic separation device. If the container means contains more than 4 main sides, then it will be appreciated by those skilled in the art that the number of flexible magnetic sheets that may be detachably secured to container means 20 may range to greater than 4 main sides. Additionally, any of such one or more flexible magnetic sheets being detachably secured to bottle means 20 may have a radially projecting portion, such as a tab means, so that the user can readily grip radially projecting tab means to facilitate pulling apart or disengaging the flexible magnetic sheet from bottle means 20 by the application of a relatively small force in utilizing a "peeling" action when it is desired to separate the flexible magnetic sheet from bottle means 20. In a further embodiment wherein the magnetic separation device comprises a container means detachably secured to at least one flexible magnetic sheet using a nonpermanent adhesive therebetween; the container means is detachably secured to one flexible magnetic sheet. However, the flexible magnetic sheet is generally dimensionally coextensive in length, width, and shape to two or more sides of the container in forming magnetic separation device. More particularly, in an example of this further embodiment, the flexible magnetic sheet could be applied as a "wrap" around a bottle means such that the flexible magnetic sheet is generally dimensionally coextensive in length, width, and shape with two or more sides of the bottle, particularly in relation to the fluid holding chamber of the bottle. Also, where the bottle is cylindrical in shape, the flexible magnetic sheet could be applied as a "wrap" that covers all or a substantial portion of the circumference of the outer surface of the fluid chamber portion of the bottle. This variation of the embodiment is particularly useful for cell culture bottles which may then be placed in a roller apparatus and incubated with gentle rotation of the bottle.

EXAMPLE 2

In this example, illustrated are various embodiments of the method according to the present invention for separating at least one subpopulation of a biological molecule of interest from a mixed population of biological molecules in a fluid by using the magnetic separation device according to the present invention. A first embodiment is a method of negative selection. In this first embodiment, the target biological molecules are separated from the fluid using the magnetic separation device according to the present invention. The fluid, depleted of the one or more subpopulations of target biological molecules ("one or more target biological molecules"), is then utilized for its intended purpose. The one or more target biological molecules are then discarded or otherwise disposed of. In a second embodiment, both negative selection and positive selection ("combination selection") are performed wherein the fluid, depleted of the one or more target biological molecules, is then utilized for its intended purpose, and the one or more isolated target biological molecules are used for their intended purpose(s).

A third embodiment is a method of positive selection using the magnetic separation device; i.e., the one or more biological molecules desired to be isolated from the fluid are isolated by positive selection. Positive selection involves separating the one or more target biological molecules from a mixed population of biological molecules present in a fluid, and then discarding the remaining unwanted (e.g., non-target) populations of biological molecules present in the fluid which are not magnetically separated. The objective of positive selection using the method and magnetic separation device according to the present invention is to isolate the one or more target biological molecules thereby obtaining relatively high yields and purity of the one or more target biological molecules. The magnetically separated one or more biological molecules may then be used for their intended purpose. Depending upon what the intended purpose is, the magnetically separated one or more biological molecules may be isolated in a manner in which all or a portion of the biological function is lost; or alternatively, may be isolated in a manner to substantially preserve biological functionality. For example, if the biological molecule is a specific cell type, and the intended purpose is to analyze that cell type by flow cytometer, it is not necessary that the cell maintain any or all of its biological function. Rather, the positively selected cells need only to retain the physical presence of the cell surface and/or internal component which is to be detected by flow cytometry. In contrast, if the target biological molecule is a cell type which is to be introduced into culture subsequent to separation, desirably the separated cells are substantially isolated in their native form; e.g., retaining substantially all of the biological function.

In general, the method of using the magnetic separation device according to the present invention involves obtaining a fluid containing a mixed population of biological molecules, from which it is desired to separate at least one subpopulation of biological molecules. For example, when a single subpopulation of biological molecules is desired to be isolated, the fluid from which it is to be isolated, and magnetic particles coated with a ligand (magnetic separation reagent) having sufficient binding specificity and affinity for the targeted subpopulation of biological molecule, are introduced into the container means of the magnetic separation device. Agitation means may be used to facilitate the contact between the magnetic separation reagent and the target biological molecule in forming complexes within the chamber of the container means. For example, if the container means comprises a bag means or a bottle means, the container means may be gently agitated either manually, or agitated automatically (e.g., using a rotator means or rocker means).

Figure 2:
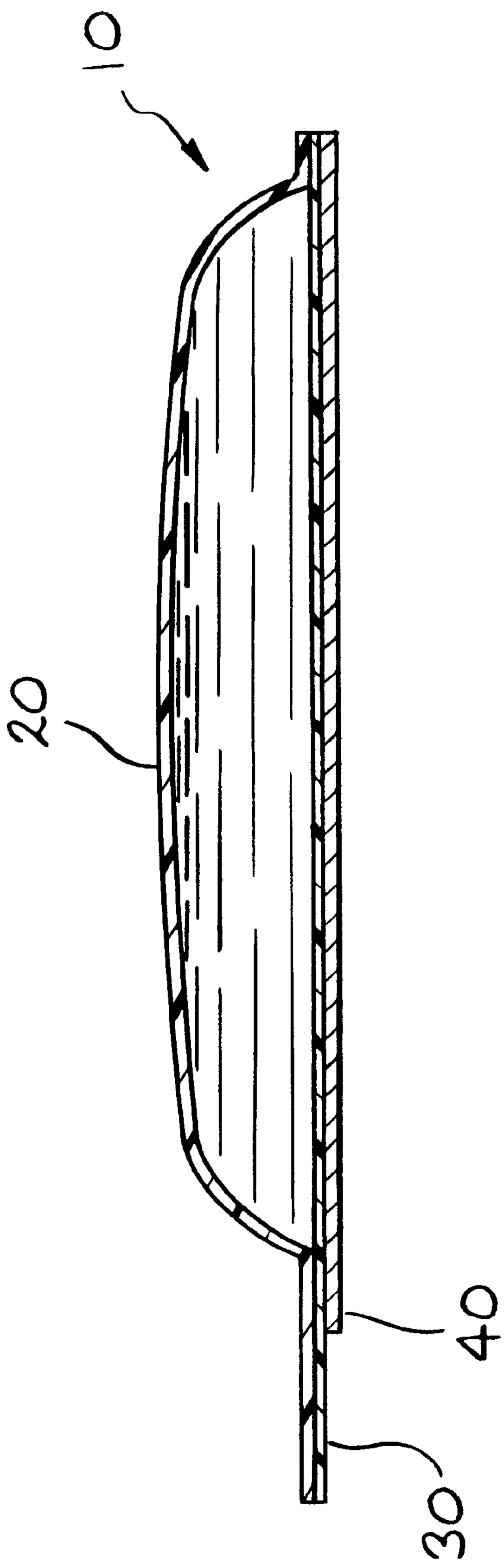
FIG. 2 is a side view in section of the magnetic separation device taken on line 2—2 of FIG. 1 showing the magnetic separation device lying on a flat surface.

In one embodiment, the magnetic separation device may be placed in a manner such that the flexible magnetic sheet means lies flat, and in contact with a supporting surface (see, e.g., FIG. 2). In one variation of this embodiment, some or all of the magnetic separation reagent may be added first so as to already be substantially held into place along, and in physical contact with, the inside surface of the fluid holding chamber of the container means adjacent to and along the dimensions of flexible magnetic sheet means; and then the fluid is added to the magnetic separation device. Alternatively, the fluid and magnetic separation may be mixed first, and then the magnetic separation device may be placed in a manner such that the flexible magnetic sheet means lies flat, and in contact with a supporting surface. After a sufficient time, the magnetic separation reagent contacts and binds to the target biological molecule present in the fluid, thereby forming complexes. These complexes contact, and are held in position along, inside of the face of container means (along the fluid holding chamber), the outer surface of which is detachably secured to the flexible magnet sheet means, because of the attraction to the magnetic field strength of the flexible magnetic sheet means. In either embodiment, or related embodiments, there is an incubation period which consists of a time period sufficient for contact and binding interactions between the magnetic separation reagent and the target biological molecule in forming complexes, and the binding of the complexes to the inside surface of the container means adjacent to and along the dimensions of flexible magnetic sheet means. It is appreciated by those skilled in the art that the incubation period may vary depending on such factors including, but not limited to, the magnetic field strength of the flexible magnetic sheet means, the amount of magnetic separation reagent relative to the amount of the target biological molecule present in the fluid, the type of magnetic particle used in forming the magnetic separation reagent, and the manner in which the incubation step is performed.

After the incubation period, the fluid is removed from the container means, e.g., via the aperture. If negative selection is being performed, the fluid (and contents therein) thereby removed comprises the desired end product. If positive selection is being performed, the fluid may be discarded since the separated target biological molecule (complexed to the magnetic separation reagent) is the desired end product. In positive selection, the inner surfaces of the container means (e.g., the fluid holding chamber) of the magnetic separation device may be washed with a buffer or solution biologically compatible with the separated target biological molecule to remove any remaining unbound or nonspecifically bound biological molecules still present inside the container means. In that regard, one or more washes may be performed by introducing the wash solution into the container means via the aperture, gently agitating the container means to rinse one or more inner surfaces (e.g., the inside surface of the container means adjacent to and along the dimensions of flexible magnetic sheet means, and to which is bound the complexes) and then removing the wash solution from the container via the aperture.

After the washing step of the positive selection process using the method according to the present invention, performed is a step in which the complexes are collected from the magnetic separation device. It will be apparent to those skilled in the art that the collection step may be performed in a number of ways. In general, the collection step involves introducing a final solution (e.g. a solution biologically compatible with the target biological molecule which is to be used for storing, and/or for use with, the target biological molecule) into the container means (e.g., via the aperture) such that the final solution is in physical contact with the complexes held into position by the flexible magnetic sheet means of the magnetic separation device; and then disengaging the flexible magnetic sheet means away from the container means by a peeling action, thereby removing the magnetic force holding the complexes into place in the container means, and thereby releasing the complexes into the final solution contained within the fluid holding chamber. The final solution, containing the separated target biological molecule, may then be removed from the container means (e.g., via the aperture), if desired.

If desired, the separated biological molecule may then be harvested from the complexes using an elution process known to those skilled in the art to depend on the type of chemical or molecular interaction between the ligand and the target biological molecule. As will be appreciated by those skilled in the art, whether elution is desirable or not will depend on such factors which include, but are not limited to, the nature of the separated target biological molecule, and its intended use subsequent to the selection process. Elution processes include, but are not limited to, changing the pH; changing the salt concentration; or adding an agent which alters the conformation of the ligand or the target biological molecule, or both; such that the separated target biological molecule is dissociated from the ligand. In one embodiment in which a degradable magnetic particle is used as a component in the magnetic separation reagent, a elution process to separate the separated target biological molecule from the magnetic particle may be obviated upon degradation of the magnetic particle. In another embodiment in which the container means comprises a cell culture bag, and the separated target biological molecule is a living cell of a desired cell type, the final solution may comprise growth medium compatible for growth of the separated cell type. In this particular embodiment, it is not necessary to remove the cells and growth medium from the container means. Rather, the container means, containing the growth medium and separated cell type, may be placed directly into an incubator supplying conditions (temperature, atmospheric) sufficient for cell growth. For many cell types, an elution process is not necessary as these cells, when attached to a magnetic particle, will still divide to form new cells during the growth process.

It will be appreciated by those skilled in the art that the above described method according to the present invention may be modified. For example, using the above-described method and magnetic separation device, instead of separating a single subpopulation of biological molecules from mixed populations of biological molecules, simultaneously separated from the fluid are more than one distinct subpopulations of target biological molecules. In one variation of this example, the magnetic separation reagent comprises (a) magnetic particles coated with a single type of ligand having multiple binding specificities (e.g., for more than one subpopulation of biological molecule); (b) magnetic particles coated with more than one type of ligand, each type of ligand differing in the binding specificity as compared to the other, thereby together binding more than one subpopulation of target biological molecule; (c) a series of magnetic particles wherein each representative species of the series is coated with a ligand having a binding specificity for a single subpopulation of target biological molecule and which is different than the binding specificity of other species in the series; and a combination thereof. Thus, by adding such a magnetic separation reagent to the fluid, and using the method and device according to the present invention, multiple distinct subpopulations of target biological molecules may be separated simultaneously from the fluid.

There are several variations by which multiple subpopulations of biological molecules may be targeted, and isolated from a fluid containing mixed populations of biological molecules, using the method and magnetic separation device according to the present invention. For brevity, the method for separating multiple subpopulations of biological molecules will mainly be described in terms of separately isolating two distinct subpopulations of target biological molecules from mixed populations of biological molecules contained in a fluid. It will be apparent from this description that the magnetic separation device and the method of using the same may be used to isolate (separately or simultaneously) more than two distinct subpopulations of target biological molecules from mixed populations of biological molecules contained in a fluid. Thus, it should be understood that the magnetic separation device and the method of using the same according to the present invention may be used to isolate more than two distinct subpopulations of target biological molecules from mixed populations of biological molecules contained in a fluid. Two or more distinct subpopulations of target biological molecules may be isolated in a single magnetic separation device; or may be separated using a series of magnetic separation devices which are physically connected in tandem, but which can be manipulated to maintain a separate container per magnetic separation device. Each magnetic separation device, in a series of magnetic separation devices, may also have at least one separate aperture specific for each respective container means.

For example, to separately isolate two distinct subpopulations of target biological molecules from mixed populations of biological molecules contained in a fluid, performed are sequential isolations thereby separating the distinct subpopulations of target biological molecules one at a time. In one illustration of this example, reference is made to FIG. 5 which shows a magnetic separation device 10 comprising container means 20 detachably secured by a non-permanent adhesive 45 to flexible magnetic sheet means 40 and 41. In continuing with this illustration, magnetic separation device 10 is turned on its side such that flexible magnetic sheet means 40 is lying substantially flat in relation to, and in physical contact with, a support surface. Introduced into the container means 20, via aperture 29, is a first magnetic separation reagent having binding specificity for a first target biological molecule such that the first magnetic separation reagent becomes substantially held into place along, and in physical contact with, the inside surface (i.e. of the fluid holding chamber) of face 30 of container means 20, and adjacent to and along the dimensions of flexible magnetic sheet means 40. After the first magnetic separation reagent is held into place as such, the magnetic separation device is rotated approximately 90 degrees such that now only flexible magnetic sheet means 41 is lying substantially flat in relation to, and in physical contact with, the support surface. Introduced into the container means 20, via aperture 29, is a second magnetic separation reagent having binding specificity for a second target biological molecule such that the second magnetic separation reagent becomes substantially held into place along, and in physical contact with, the inside surface (i.e. of the fluid holding chamber) of face 31 of container means 20, and adjacent to and along the dimensions of flexible magnetic sheet means 41. The result to this point is magnetic separation device 10 having bound onto one inner surface the first magnetic separation reagent, and having bound onto another inner surface the second magnetic separation reagent. Now, the fluid having a mixed population of biological molecules, from which is to be isolated the first and second target biological molecules, is introduced into the container means 20 (e.g., via aperture 29) of magnetic separation device 10. Magnetic separation device 10 is placed on its side, and substantially flat, and then gently rotated from side to side such that physical contact by the fluid is alternated between the bound first magnetic separation reagent and the bound second magnetic reagent. For example, magnetic separation device 10 is first positioned such that flexible magnetic sheet means 40 is lying substantially flat in relation to, and in physical contact with, the support surface. The fluid is then in contact with substantially only the first magnetic separation reagent (along inner surface of face 30). The magnetic separating device is then rotated 90 degrees such that the fluid is then in contact with substantially only the second magnetic separation reagent (along inner surface of face 31). The rotation of the magnetic separation device 10 may be continued for a sufficient time such that the first magnetic separation reagent contacts and binds to the first target biological molecule present in the fluid, thereby forming a first set of complexes; and the second magnetic separation reagent contacts and binds to the second target biological molecule present in the fluid, thereby forming a second set of complexes. The first set of complexes contact, and are held in position along, the inner surface of face 30; whereas the second set of complexes contact, and are held in position along, the inner surface of face 31. The fluid is then removed from container means 20 (e.g., via aperture 29). If negative selection is being performed, the fluid (and contents therein) thereby removed comprises the desired end product. If positive selection is being performed, the fluid may be discarded, since the two separated target biological molecules (held in their respective positions in the fluid holding chamber of container means 20) are the desired end products. In positive selection, the inner surfaces of the container means (e.g., the fluid holding chamber) of the magnetic separation device may be washed with a buffer or solution biologically compatible with the separated target biological molecules to remove any remaining unbound or nonspecifically bound (e.g., non-target) biological molecules still present inside the container means. In that regard, one or more washes may be performed by introducing a wash solution into the container means via the aperture, gently agitating the container means to rinse the inner (inside) surfaces of the container means (and thus also contacting, and washing both the first and second sets of complexes held in their respective positions). After each wash step, the wash solution is removed from the container means (e.g., via the aperture).

After the washing step of the positive selection process using the method according to the present invention, performed is a collection step in which the first and second sets of complexes are separately collected from the magnetic separation device. It will be apparent to those skilled in the art that the collection step may be performed in a number of ways. In continuing with this particular illustration, the collection step involves introducing a first final solution (e.g. a solution biologically compatible with the first target biological molecule which is to be used for storing, and/or for use with, the first target biological molecule) into the container means (e.g., via the aperture) such that the first final solution is in substantial physical contact with the first set of complexes held into position by the flexible magnetic sheet means 40 of the magnetic separation device. Flexible magnetic sheet means 40 is then disengaged from container means 20 by a peeling action, thereby removing the magnetic force holding the first set of complexes into place in the container means, and thereby releasing the first set of complexes into the first final solution contained within the fluid holding chamber. The first final solution, containing the separated first target biological molecule, may then be removed from the container means (e.g., via the aperture). Optionally, a second wash step may be performed to substantially remove any traces of the first target biological molecule before the collection step proceeds to the process of removing the second set of complexes (containing the separated second target biological molecule).

In continuing with this illustration of the collection step, a second final solution (e.g. a solution biologically compatible with the second target biological molecule which is to be used for storing, and/or for use with, the second target biological molecule) is introduced into the container means (e.g., via the aperture) such that the second final solution is in substantial physical contact with the second set of complexes held into position by the flexible magnetic sheet means 41 of the magnetic separation device. Flexible magnetic sheet means 41 is then disengaged from container means 20 by a peeling action, thereby removing the magnetic force holding the second set of complexes into place in the container means, and thereby releasing the second set of complexes into the second final solution contained within the fluid holding chamber. The second final solution, containing the separated second target biological molecule, may then be removed from the container means (e.g., via the aperture). As already described in detail herein, if desirable, the separated first target biological molecule or the separated second target biological molecule may then be harvested from their respective complexes using an elution process known to those skilled in the art.

EXAMPLE 3

Presented in this example are illustrations of the functioning of the magnetic separation device according to the present invention. Into a volume of 20 ml of phosphate buffered saline (PBS) was suspended $10^6$ magnetic particles/ml of a commercially available magnetic particle (DYNABEAD M-450 coated with a polymer and avidin). The 20 ml suspension was then introduced into a magnetic separation device similar to that illustrated in FIG. 1. The magnetic separation device, containing the suspension, was turned on its side such that the flexible magnetic sheet means was lying substantially flat in relation to, and in physical contact with, a support surface. In such a position and with gentle agitation, the magnetic separation device was incubated at room temperature for 5 minutes. After the incubation, the fluid was removed from the magnetic separation device. For determining the percentage of magnetic particles retained in the magnetic separation device, an aliquot of the removed fluid was placed in a hemacytometer, and the magnetic particles were counted using a light microscope. The results indicated that the removed solution contained less than one magnetic particle per ml of solution. Thus, less than 0.0001% of the magnetic particles were lost in a negative selection process using the magnetic separation device according to the present invention.

In another illustration, a suspension comprising 20 ml of PBS and $2\times10^7$ particles ($10^6$ particles/ml) was introduced into a magnetic separation device, the magnetic separation device was then turned on its side such that the flexible magnetic sheet means was lying substantially flat in relation to, and in physical contact with, a support surface. In such a position and with gentle agitation, the magnetic separation device was incubated at room temperature for 5 minutes. After the incubation, the fluid was removed from the magnetic separation device. A wash was performed by introducing a wash solution (20 ml PBS) into the container portion of the magnetic separation device, gently agitating the magnetic separation device for 30 seconds, and then removing the wash solution. Two additional wash steps were performed in the same manner. A final solution (20 ml PBS) was then introduced into the magnetic separation device, the flexible magnetic sheet means was peeled away and removed from contact with the container means, and the container means was then gently agitated for a few minutes. For determining the percentage of magnetic particles recovered in the final solution, an aliquot of the removed final solution was placed in a hemacytometer, and the magnetic particles were counted using a light microscope. The results indicated that the removed final solution contained $8.5\times10^5$ magnetic particles/ml (total of $1.7\times10^7$ magnetic particles). Thus, 85% of the magnetic particles were recovered in a positive selection process using the magnetic separation device according to the present invention.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the appended claims.

What is claimed is:

1. A magnetic separation device for separation of one or more biological molecules in a fluid, wherein the magnetic separation device comprises: a container comprising a chamber capable of holding the fluid; a flexible magnetic sheet; and a non-permanent adhesive that coats a surface selected from the group consisting of an outer surface of the container, a face of the flexible magnetic sheet, and a combination thereof; wherein by the non-permanent adhesive, detachably secured in a face to face manner to the outer surface of the container is the flexible magnetic sheet in forming the magnetic separation device.

2. The magnetic separation device of claim 1, wherein the outer surface of the container, to which is applied the flexible magnetic sheet, comprises a flat surface.

3. The magnetic separation device of claim 1, wherein the flexible magnetic sheet and the outer surface of the container to which it is detachably secured are generally dimensionally coextensive in length, width, and shape.

4. The magnetic separation device of claim 1, wherein the magnetic separation device comprises a single unit.

5. The magnetic separation device of claim 1, wherein the magnetic separation device comprises a multiple unit, wherein the multiple unit comprises a plurality of the magnetic separation devices physically connected in tandem.

6. The magnetic separation device of claim 1, wherein the magnetic separation device comprises a multiple unit, wherein the multiple unit comprises the magnetic separation device and a plurality of containers physically connected in tandem.

7. The magnetic separation device of claim 1, wherein the flexible magnetic sheet further comprises a tab means.

8. The magnetic separation device of claim 1, wherein the non-permanent adhesive coats the outer surface of the container.

9. The magnetic separation device of claim 1, wherein the non-permanent adhesive coats the face of the flexible magnetic sheet.

10. The magnetic separation device of claim 1, wherein the non-permanent adhesive coats both the outer surface of the container and the face of the flexible magnetic sheet.

11. The magnetic separation device of claim 1, wherein the container comprises a bag means comprising a walled housing means.

12. The magnetic separation device of claim 11, wherein a portion of the bag means extends beyond the dimensional margins of the detachably secured flexible magnetic sheet, and wherein the extended portion of the bag means is accessible for gripping by a user.

13. The magnetic separation device of claim 1, wherein the container is selected from the group consisting of a bottle, and a flask.

14. The magnetic separation device of claim 13, wherein the container comprises a bottle having a fluid chamber; wherein the bottle is cylindrical in shape; and wherein the flexible magnetic sheet is applied to cover all or a substantial portion of the circumference of the outer surface of the bottle surrounding the fluid chamber.

15. A magnetic separation device of claim 1, further comprising a container having detachably secured thereto, in a face to face manner, multiple flexible magnetic sheets; wherein more than one outer surface of the container has detachably secured thereto a flexible magnetic sheet; and wherein the non-permanent adhesive coats surfaces selected from the group consisting of more than one outer surface of the container, a face of each of the multiple flexible magnetic sheets, and a combination thereof.

16. The magnetic separation device of claim 15, wherein each of the multiple flexible magnetic sheets is generally dimensionally coextensive in length, width, and shape to the outer surface of the container to which the flexible magnetic sheet is detachably secured.

17. The magnetic separation device of claim 15, wherein the magnetic separation device comprises a single unit.

18. The magnetic separation device of claim 15, wherein the magnetic separation device comprises a multiple unit, wherein the multiple unit comprises a plurality of the magnetic separation devices physically connected in tandem.

19. The magnetic separation device of claim 15, wherein the magnetic separation device comprises a multiple unit, wherein the multiple unit comprises the magnetic separation device and a plurality of containers physically connected in tandem.

20. The magnetic separation device of claim 15, wherein the each of the multiple flexible magnetic sheet further comprises a tab means.

21. The magnetic separation device of claim 15, wherein the non-permanent adhesive coats the more than one outer surfaces of the container.

22. The magnetic separation device of claim 15, wherein the non-permanent adhesive coats the face of each of the multiple flexible magnetic sheets.

23. The magnetic separation device of claim 15, wherein the non-permanent adhesive coats a combination of the more than one outer surface of the container, and a face of each of the multiple flexible magnetic sheets.

24. The magnetic separation device of claim 15, wherein the container comprises a bag means comprising a walled housing means.

25. The magnetic separation device of claim 15, wherein the container is selected from the group consisting of a bottle, and a flask.

26. A magnetic separation device of claim 1, further comprising a container having detachably secured thereto, in a face to face manner, a single flexible magnetic sheet; wherein more than one outer surface of the container has detachably secured thereto the flexible magnetic sheet; and wherein the non-permanent adhesive coats surfaces selected from the group consisting of more than one outer surface of the container, a face of the flexible magnetic sheet, and a combination thereof.

27. The magnetic separation device of claim 26, wherein the non-permanent adhesive coats the more than one outer surfaces of the container.

28. The magnetic separation device of claim 26, wherein the non-permanent adhesive coats the face of the flexible magnetic sheet.

29. The magnetic separation device of claim 26, wherein the non-permanent adhesive coats a combination of the more than one outer surface of the container, and the face of the flexible magnetic sheet.

30. A method for making a magnetic separation device according to claim 1 comprising:

(a) applying a non-permanent adhesive to coat a surface selected from the group consisting of an outer surface of the container, a face of the flexible magnetic sheet, or a combination thereof;

(b) contacting the outer surface of the container and the face of the flexible magnetic sheet in a face to face manner; and (c) applying pressure to the container and flexible magnetic sheet where they are dimensionally coextensive to detachably secure the container to the flexible magnetic sheet in forming the magnetic separation device.

31. The method according to claim 30, wherein the non-permanent adhesive is applied to the outer surface of the container.

32. The method according to claim 30, wherein the non-permanent adhesive is applied to the face of the flexible magnetic sheet.

33. The method according to claim 30, wherein the non-permanent adhesive is applied to both the outer surface of the container and the face of the flexible magnetic sheet.

34. The method according to claim 30, wherein the container comprises a bag means.

35. The method according to claim 30, wherein the container is selected from the group consisting of a bottle, and a flask.

36. A method of using the magnetic separation device according to claim 1 for separating by positive selection a subpopulation of biological molecules present in a fluid containing a mixed population of biological molecules, the method comprising the steps of:

(a) obtaining the fluid containing a mixed population of biological molecules;

(b) mixing the fluid containing the mixed population of biological molecules with a magnetic separation reagent having sufficient binding specificity and affinity for the subpopulation of biological molecules;

(c) contacting the mixture from step (b) with the fluid holding chamber of the container of the magnetic separation device;

(d) incubating for a sufficient time for the magnetic separation reagent to contact and bind to the subpopulation of biological molecules thereby forming complexes, if the subpopulation of biological molecules is present;

(e) placing the magnetic separation device in a manner such that the flexible magnetic sheet means lies flat, and in contact with a supporting surface thereby allowing complexes formed to be held in position because of magnetic attraction of the magnetic separation reagent to the flexible magnetic sheet;

(f) removing the fluid from the container;

(g) performing at least one wash step, wherein the wash step comprises adding a wash solution to the container and rinsing inner surfaces of the fluid holding chamber with the wash solution, and removing the wash solution from the container; and (h) performing a collection step, wherein the collection step comprises introducing a final solution into the container, disengaging the flexible magnetic sheet away from the container by a peeling action, thereby releasing the complexes containing the separated subpopulation of biological molecules into the final solution.

37. The method according to claim 36, wherein the fluid containing the mixed population of biological molecules, and the magnetic separation reagent are mixed prior to introduction into and contact with the chamber of the container of the magnetic separation device.

38. The method according to claim 36, wherein the fluid containing the mixed population of biological molecules, and the magnetic separation reagent are each separately introduced into, and then mixed inside the chamber of the container of the magnetic separation device.

39. The method according to claim 36, wherein the more than one wash step is performed.

40. The method according to claim 36, further comprising an elution step after step (h), wherein the elution step comprises eluting the separated subpopulation of biological molecules from the magnetic separation reagent by treating the complexes to dissociate the biological molecules from the magnetic separation reagent.

41. A method of using the magnetic separation device according to claim 15 for separating by positive selection multiple subpopulations of biological molecules present in a fluid containing a mixed population of biological molecules, the method comprising the steps of:

(a) obtaining the fluid containing a mixed population of biological molecules;

(b) adding a first magnetic separation reagent, having binding specificity for a first subpopulation of biological molecules to be separated, into the container of the magnetic separation device;

(c) placing the magnetic separation device in a manner such that a first flexible magnetic sheet means lies flat, and in contact with a supporting surface, and for a sufficient time in which the first magnetic separation reagent is bound in position in the container because of its magnetic attraction to the first flexible magnetic sheet;

(d) rotating the position of the magnetic separation device in a manner such that a second flexible magnetic sheet means lies flat, and in contact with the supporting surface;

(e) adding a second magnetic separation reagent, having binding specificity for a second subpopulation of biological molecules to be separated, into the container of the magnetic separation device so that the second magnetic separation reagent is bound in position in the container because of its magnetic attraction to the second flexible magnetic sheet;

(f) adding the fluid containing the mixed population of biological molecules into the container;

(g) gently rotating the magnetic separation device from side to side such that physical contact by the fluid is alternated between the first bound magnetic separation reagent and the second bound magnetic separation reagent, and incubating for a sufficient time for the first bound magnetic separation reagent to contact and bind to the first subpopulation of biological molecules to be separated thereby forming a first set of complexes, and for the second bound magnetic separation reagent to contact and bind to the second subpopulation of biological molecules to be separated thereby forming a second set of complexes;

(h) removing the fluid from the container;

(i) performing at least one wash step, wherein the wash step comprises adding a wash solution to the container and rinsing inner surfaces of the fluid holding chamber with the wash solution, and removing the wash solution from the container;

(j) performing a first collection step, wherein the first collection step comprises introducing a first final solution into the container, disengaging the first flexible magnetic sheet away from the container by a peeling action, thereby releasing the first set of complexes containing the first separated subpopulation of biological molecules into the first final solution, and removing the first final solution containing the first set of complexes from the container; and (k) performing a second collection step, wherein the second collection step comprises introducing a second final solution into the container, disengaging the second flexible magnetic sheet away from the container by a peeling action, thereby releasing the second set of complexes containing the second separated subpopulation of biological molecules into the second final solution, and removing the second final solution containing the second set of complexes from the container.

42. The method according to claim 41, wherein the more than one wash step is performed.

43. The method according to claim 41, further comprising an elution step, wherein complexes selected from the group consisting of the first set of complexes, the second set of complexes, and the first set of complexes and the second set of complexes, are treated to dissociate the separated subpopulation of biological molecules from the magnetic separation reagent.

44. A method of using the magnetic separation device according to claim 1 for separating by negative selection a subpopulation of biological molecules present in a fluid containing a mixed population of biological molecules, the method comprising the steps of:

(a) obtaining the fluid containing a mixed population of biological molecules;

(b) mixing the fluid containing the mixed population of biological molecules with a magnetic separation reagent having sufficient binding specificity and affinity for the subpopulation of biological molecules to be removed;

(c) contacting the mixture from step (b) with the fluid holding chamber of the container of the magnetic separation device;

(d) incubating for a sufficient time for the magnetic separation reagent to contact and bind to the subpopulation of biological molecules thereby forming complexes, if the subpopulation of biological molecules is present;

(e) placing the magnetic separation device in a manner such that the flexible magnetic sheet means lies flat, and in contact with a supporting surface thereby allowing complexes formed to be held in position because of magnetic attraction of the magnetic separation reagent to the flexible magnetic sheet; and (f) removing the fluid from the container, wherein the fluid is depleted of the subpopulation of biological molecules to be removed.

45. The method according to claim 44, wherein the fluid containing the mixed population of biological molecules, and the magnetic separation reagent are mixed prior to introduction into and contact with the chamber of the container of the magnetic separation device.

46. The method according to claim 44, wherein the fluid containing the mixed population of biological molecules, and the magnetic separation reagent are each separately introduced into, and then mixed inside the chamber of the container of the magnetic separation device.

* * * * *